United States Patent [19]

Kater

[11] 4,340,457
[45] Jul. 20, 1982

[54] ION SELECTIVE ELECTRODES

[76] Inventor: John A. R. Kater, 2037 W. San Lorenzo, Santa Ana, Calif. 92704

[21] Appl. No.: 116,297

[22] Filed: Jan. 28, 1980

[51] Int. Cl.³ .............................................. G01N 27/30
[52] U.S. Cl. ................................ 204/195 R; 128/635; 204/195 M; 204/195 F
[58] Field of Search .......... 204/195 F, 195 M, 195 R; 128/635

[56] References Cited

U.S. PATENT DOCUMENTS

| 3,824,157 | 7/1974 | Macur | 204/1 T |
| 3,856,649 | 12/1974 | Genshaw et al. | 204/195 F |
| 4,197,852 | 4/1980 | Schindler et al. | 128/635 |
| 4,214,968 | 7/1980 | Battaglia et al. | 204/195 M |
| 4,263,343 | 4/1981 | Kim | 204/195 M X |

FOREIGN PATENT DOCUMENTS 2912834 10/1979 Fed. Rep. of Germany ... 204/195 F

OTHER PUBLICATIONS

Hackh's Chemical Dictionary, pp. 529, 612 & 637, Fourth Edition, (1972).
T. Treasure et al., J. Medical Engineering & Technology, pp. 271-273, vol. 1, No. 5, Sep. 1977.

Primary Examiner—G. L. Kaplan
Attorney, Agent, or Firm—Grover A. Frater

[57] ABSTRACT

An ion selective electrode capable of production in miniaturized form suitable for in vivo monitoring is produced by coating a metal-metal salt half cell with a layer of hydrophilic material containing electrolyte with an over-layer of an ion selective membrane. The coatings may be applied by a dipping and drying process. Stability is enhanced by addition of silver black and platinum black to the half cell and those materials may be added as layers in a similar dip and dry process. A companion reference electrode half cell is made of the same materials that are used in making the "half cell" portion of the selective electrode, except that the reference half cell is coated with a protein layer. Special packaging and a special procedure facilitate calibration.

15 Claims, 12 Drawing Figures

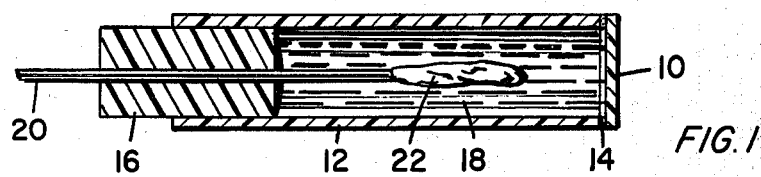
FIG. 1
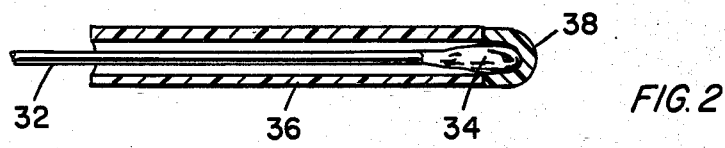
FIG. 2
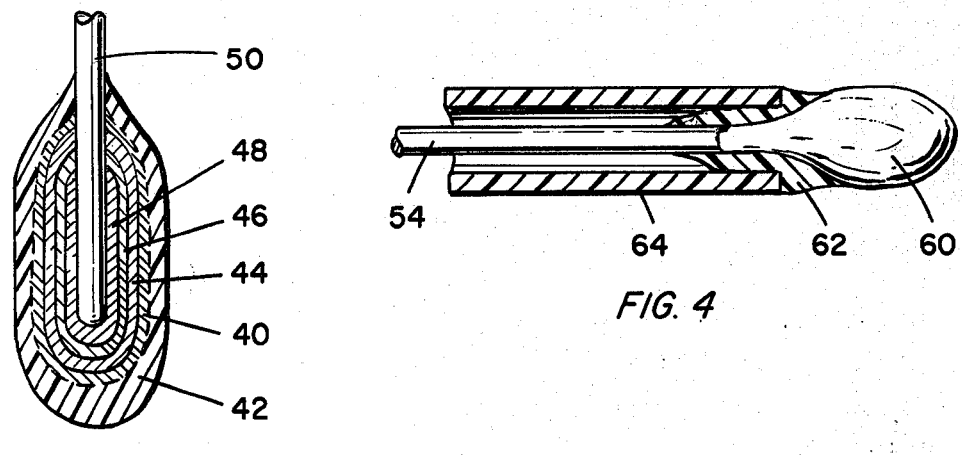
FIG. 3
FIG. 4
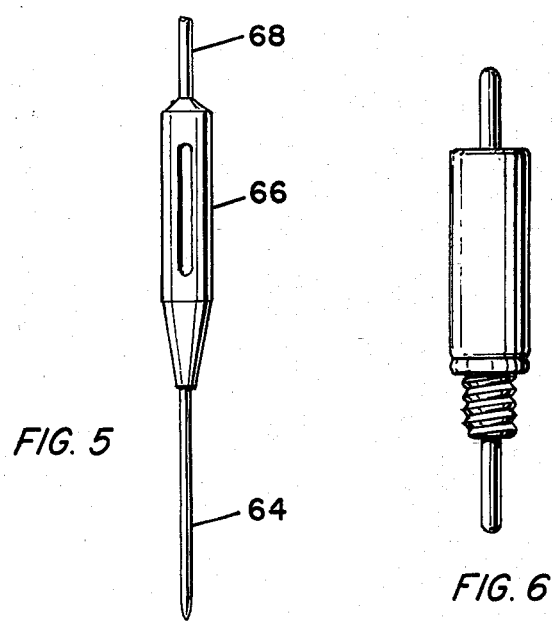
FIG. 5
FIG. 6

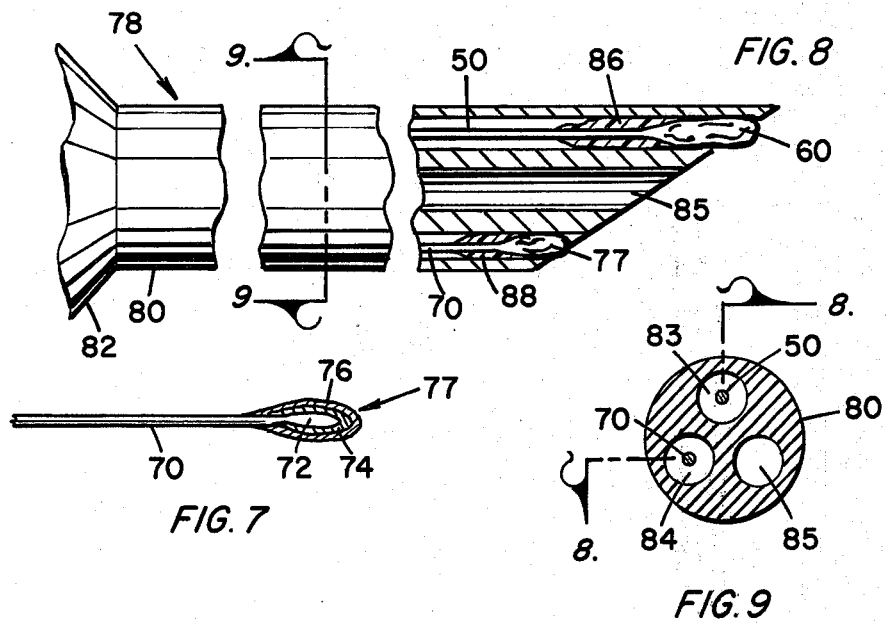
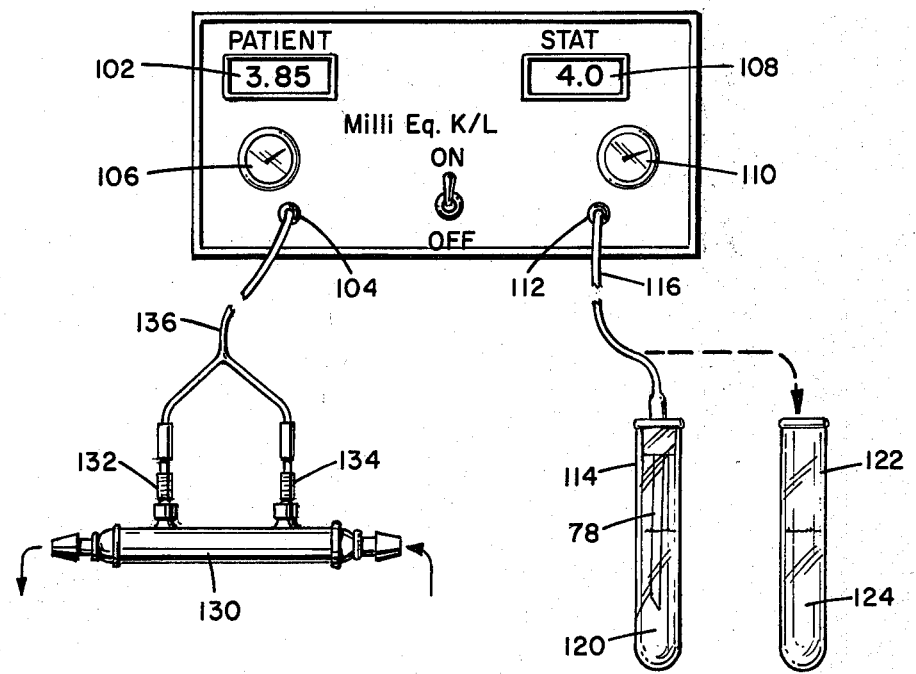

ION SELECTIVE ELECTRODES

FIELD OF THE INVENTION

This invention relates to improvements in ion selective electrodes and reference electrodes, and it relates in particular to structures and materials and techniques to be employed in producing such electrodes and in using them.

BACKGROUND OF THE INVENTION

In caring for the critically ill patient, laboratory data should be available rapidly and, preferably, continuously. Blood electrolytes such as potassium, sodium, calcium and chloride are important elements. Of particular importance is the ability to measure ionized potassium continuously (in vivo) or at least rapidly (in vitro) to provide real-time data to the physician. The gradient of potassium across the cell membrane is the principal contributor to the membrane potential. Maintenance of this electrical potential is essential for normal function of all nervous and muscular tissue, including the conducting and contracting elements of the heart. The continuous or rapid measurement of potassium ion is important in intensive care, postcardiopulmonary bypass, cardioplegia, the administration of digitalis and diuretics; acute myocardial infarction, renal failure and the treatment of burn patients and diabetic patients. A thin, catheter-mounted potassium electrode is not commercially available.

Many applications for ion selective electrodes have gone unsatisfied in the past for lack, not only of adequately selective sensing elements, but also because of difficulty in packaging the liquid elements of the measuring system. There are many examples but, selecting one of the above-mentioned conditions, there is a need to monitor potassium level in the blood of patients during and after major surgical procedures or during dialysis. It is a costly process to draw a blood sample every fifteen minutes or so and to have it analyzed in the hospital laboratory. More important, potassium level can change to critical value in less time than the time required to draw the sample, carry it to the laboratory, conduct the test, and report back to the operating team.

The situation could be greatly improved by provision of in vivo monitoring, but to do that requires a sensor that is small enough for insertion into a blood vessel. There has been no such sensor. Attempts to reduce the size of sensors necessarily involve reductions in the amount of electrolyte solution in the electrode. Heretofore, the result of such size reduction has been inaccuracy, and need for frequent recalibration due to drifting potentials.

Electrodes containing a liquid electrolyte can become a hazard to the patient should the sensing membrane, separating the electrolyte from the patient's blood, burst.

Aside from problems in miniaturization, such liquid filled electrodes cannot be sterilized by accepted sterilization procedures, such as ethylene oxide treatment, autoclaving and gamma radiation. These accepted sterilization procedures render such liquid filled electrodes inoperative by one or a combination of:

(1) physical damage to the ion sensitive membrane;
(2) physical damage to other components of the electrode (sealing structure);
(3) alteration of the chemical characteristics of the liquid electrolyte;
(4) alteration of the ion selective properties of the sensing membrane.

Prior art efforts at miniturization have produced an electrode formed by cementing discs of ion selective membrane on the end of 3 mm outside diameter polyvinyl chloride tubes, filled with 3 molar KCl and fitted with a silver wire ( D. M. Band, J. Kratochvil and T. Treasure, *Journal of Physics* 265.5-6P, 1977). Units that small have not been commercially available. The problems that attend fastening a tiny disc of membrane material to the end of a tiny tube have not been solved. Even in 5 to 12 mm diameter sizes, electrodes of that design cost several hundreds of dollars.

It is necessary when using an ion selective electrode to use a reference electrode of steady potential in the measuring system. Like the selective electrode, the reference electrode includes a body of electrolyte and a half cell. Instead of a selective membrane, it includes a "salt bridge," but like the selective electrode, it has been large and cumbersome. In some applications requiring a miniaturized selective electrode, it matters little if the reference electrode is large, but in other applications there is a need for a miniaturized reference electrode. In still other applications there is need for a miniaturized reference device even if the selective electrode is not small.

SUMMARY OF THE INVENTION

It is an object of this invention to provide an improved ion selective electrode and an improved method for making ion selective electrodes.

It is also an object to provide miniaturized ion selective electrodes which are stable under a wide range of environmental conditions and for long periods. In this connection, it is an object to provide an ion selective electrode that may be made in a form small enough and stable enough to be used in vivo, particularly during and following surgical procedures or renal dialysis.

These and other objects and advantages of the invention will be apparent upon an examination of the specification that follows and of the accompanying drawings. They result from several inventive features considered alone and, surprisingly, in combination.

In the invention, a means is provided for containing a layer of liquid in immobilized form between an ion selective membrane and the half cell segment of the electrical path. That means may comprise, and in preferred form does comprise, a membrane or layer of hydrophilic material interposed between the sensitive membrane and the half cell. An electrolyte is contained in the hydrophilic layer. The electrolyte may be trapped in place by the ion selective membrane during the manufacturing process or, if preferred, in a given application the electrolytic layer may be formed by the hydration of a hydrophilic layer and the selective membrane, as the sensor is soaked in preparation for use or at the point of manufacture.

The use of such a hydrophilic layer, which upon hydration becomes an electrolyte of defined composition, volume and spatial distribution, permits manufacture of satisfactory miniature sensors, especially when the selective membrane is formed from a liquid by painting or dipping. The electrical performance of such sensors is improved to a point equivalent to the most stable prior art sensors by the use of silver black and platinum black together with the conventional silver and silver chloride half cell materials. Silver black and platinum black appear to improve the electrical stability of the half cell materials generally. They enhance the performance of miniature electrodes when layers of such materials are added between the hydrophilic material and the half cell salt.

Other improvements which have been observed are:
(1) a drastic increase in response time from ten seconds to milliseconds—an increase of about 100 times;
(2) in the case of potassium and calcium electrodes, a 99 to 100 percent NERNST response;
(3) the electrode can be repeatedly ethylene oxide or gamma radiation sterilized without effecting the stability or performance of the electrode;
(4) the electrode may be stored wet or dry.

Electrodes with a tip diameter of 0.75 mm have been fabricated, with a rigid or flexible shaft ranging in length from 2 cm to 60 cm.

The invention extends to the use of particular preferred materials and preferred structural forms and preferred production methods which are described below in connection with the description of the best mode known to application for practicing the invention.

The invention also provides a novel method for using miniature ion selective electrodes, and in this connection it provides a new, miniature reference electrode and a new combination electrode.

While it need use only one, the preferred form of the method utilizes a two-channel direct reading analyzer for continuous inter- and intravascular monitoring of blood electrolytes also presents a calibration problem. Electrodes placed in a blood vessel (intervascular) or in a bypass loop (extravascular) cannot be taken out and replaced for calibration or a calibration check during surgery or in the intensive care ward. Such a method would be time consuming, traumatic, and create a potential for bacterial contamination, even if the calibrating solutions were sterilized.

To solve these problems, an in vivo or in-line calibration method is employed using a dual channel analyzer as follows:

(1) The sterile catheter combination electrode is placed in a venous blood vessel of the patient and the electrode lead connected to the patient channel of the analyzer;
(2) The stat combination electrode is placed in a standard solution (which need not be sterile) of 4.0 milliequivalents K/L and the electrode lead is connected to the stat channel of the analyzer;
(3) The reading on the stat channel is now adjusted to read 4.0;
(4) A blood sample is drawn (venous blood) from the patient and transferred to a test tube;
(5) The potassium content of the blood sample is measured with the calibrated stat electrode;
(6) Finally, the patient channel is adjusted to read the same value as the stat channel.

For example, if the fresh blood sample reads 2.57 on the stat channel using the stat electrode, adjust the patient channel to read 2.57. To recheck the calibration of the indwelling catheter electrode, simply repeat steps (4), (5) and (6). This simple and reliable calibration method takes no more time than a few seconds.

The difference between that method and the prior art method can be understood by considering how they are applied to the measurement of potassium in the blood of a patient during and after surgery. In the prior method, a blood sample was drawn from the patient just prior to commencement of the surgery. The sample was labelled and then carried from the operating room to the hospital's laboratory where the potassium content was measured. A report was prepared which was carried or reported by telephone back to the operating room. The elapsed time from drawing the sample to return of the report was typically twenty minutes. In a usual case, a new blood sample was taken and analyzed about every twenty minutes. The process was continued after the patient was moved from operating room to the intensive care unit, except that measurement frequency was usually reduced.

In the method of the invention, the ion selective and reference electrodes are inserted together, as separate units or as a combination electrode, into the patient's blood. They may be inserted into the flow through a by-pass or directly into a vein. Those electrodes are connected to the measuring channel of the dual channel analyzer. Another selective electrode and reference electrode pair are connected to the calibration channel of the instrument and are inserted in a standard potassium solution. The reference channel is adjusted until the reference display indicates the potassium content of the standard solution. A sample of the patient's blood is drawn. The ion sensitive electrode and the reference electrode of the calibration pair are moved from the standard solution to the blood sample. The display indication is noted and the measuring channel is then adjusted to provide that same indication. If the physician has any doubt about the accuracy of the reading on the measurement display, he need only draw a blood sample and measure it with the calibration electrodes. Agreement of the measurement and calibration display indications is evidence that the measurement is accurate.

By this new method, the potassium measurements are continuous and current, and the cost of making the measurements is generally much less than the cost of a half dozen or more laboratory tests of blood samples. Two channel analyzers need not be expensive. They can be small, light-weight, and easily portable. It is entirely feasible to move the analyzer and the electrodes with the patient from operating room to the intensive care unit or elsewhere.

The method provides another very special benefit. The two electrode sets are subjected to the same sample material. The fluids of the body have the same effectiveness as an electrolyte everywhere in the body. Any variation will be so minor as to make no practical difference. Since the reference electrode used for measurement and calibration will be subjected to the same electrolyte, there is no need to provide a standard KCl or other electrolyte. When the method of the invention is employed, the conventional salt bridge and the electrolyte body can be eliminated. The two reference electrodes become no more than a silver wire with a small amount of silver chloride bonded to the wire at the end or other point that will be immersed in the blood or other body fluid.

The silver wire may be very thin, indeed, and the silver chloride no more than a spec at the end of the wire. Not only has the physical size been reduced, but so has the cost. Now a combination electrode can be considered to be disposable and it is a feature of the invention to provide an improved reference electrode and an improved combination electrode for use in the method.

The materials employed in the reference half cell are the same, in the preferred embodiment, as are used in the "half cell" portion of the ion selective electrode. If silver, silver chloride, silver black, and platinum black are included in one, they should be included in the other.

Further, to insure that the reference electrode does not undergo a calibration shift when placed in the test solution, as a consequence of "poisioning," it is prepoisioned by soaking for an hour or two in an animal protein when intended for measurements in blood.

Also, to insure that there is no need for a presoaking period prior to use, the electrodes are packaged in a controlled environment. They are packaged with their active, electrode surfaces in a reference or calibration solution. The remainder, except for electrical leads to be used for calibration in the package, is contained in a sealed, sterile package.

THE DRAWINGS

In the drawing:

FIG. 1 is a cross-sectional, schematic showing of part of a prior art ion selective electrode;

FIG. 2 is a cross-sectional, schematic view of another electrode which incorporates some features of this invention;

FIG. 3 is a greatly enlarged cross-sectional, schematic view of still another sensor structure which incorporates additional features of the invention;

FIG. 4 is a cross-sectional view illustrating how the sensor of FIG. 3 is mounted to produce a needle like structure;

FIG. 5 is an elevational view of an electrode which embodies the sensor of FIGS. 3 and 4 and is useful for in vivo monitoring of potassium in blood;

FIG. 6 is an elevational view of a sensor which embodies the invention and is made for industrial applications;

FIG. 7 is a cross-sectional view of a reference electrode for use in the invention;

FIG. 8 is a cross-sectional view of a combination electrode which combines the electrode structures of FIGS. 4 and 7;

FIG. 9 is a cross-sectional view taken on line 9—9 of FIG. 8;

FIG. 10 is a diagram illustrating how the sensor sets and the analyzer are arranged in practicing the method of the invention;

DETAILED DESCRIPTION

Figure 11:
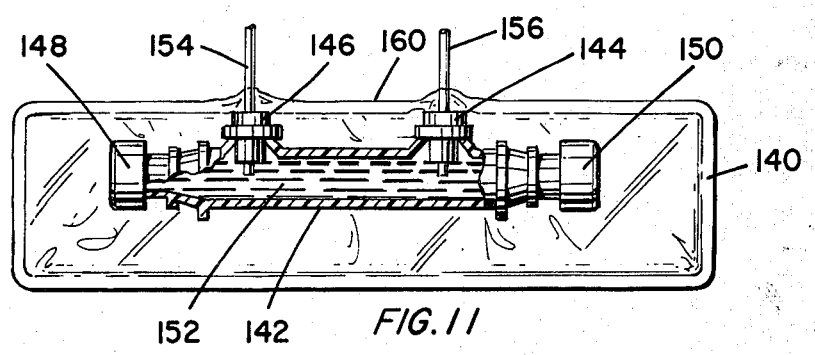
FIG. 11 is a view in front elevation, and partly in section, of a pair of sensors disposed in a reference solution and in a sterile package.

The invention is applicable to ion selective electrodes other than potassium electrodes, and it is applicable to sensors in a wide range of physical sizes and shapes. However, the invention solves what has been a difficult and limiting problem in that it makes possible in vivo sensing of potassium using the best potassium selective materials that are currently available. In vivo sensing of potassium is the best known mode for practicing the invention and that mode has been selected for detailed description here.

The best potassium ion selective membrane currently available appears to be the membrane described by D. M. Bank, J. Kratochvil and T. Treasure in the *Journal of Physics*, volume 265, published in 1977 at pages 5 and 6. The membrane is formed by dissolving the following list of ingredients in 3 ml of tetrahydrofuran and then evaporating the solvent material.

Valinomycin—0.00015 grams
Bis-2-ethylhexyladipate—0.15 grams
Nitrobenzene—0.05 grams
Potassium tetraphenylborate—0.000025 grams
High molecular weight PVC—0.075 grams The product of that process is a PVC membrane essentially hydrophobic, whose hardness or flexibility is a function of the density and quantity of the constituent PVC and the plasticizer. For convenience, the material is sometimes referred to herein as PVC or potassium selective PVC.

Conventionally, this PVC material is formed into a thin membrane, cut discs of which are glued to the end of a PVC tube. The interior of the tube is filled with an electrolyte. The electrolyte is usually a solution containing KCl. A half cell is immersed in the electrolyte. The half cell may be formed by dipping a silver wire in molten silver chloride. An electrode thus described is shown in FIG. 1 of the drawing.

The ion selective PVC membrane 10 is secured to the end of tube 12 by a polymer adhesive shown as a thin annulus 14 at the end of the PVC tube.

A plug 16 inside the tube at a point removed from the membrane serves to retain the body 18 of electrolyte in contact with the membrane 10. A chlorided silver wire 20 extends through the plug into the electrolyte to form a half cell 22. The electrolyte is a solution of potassium chloride. Such an electrode, in this and other physical forms, has proven to be a stable measuring instrument. Such electrodes are commercially available in tubular form. Typical diameters are 5 mm to 12 mm. Typical life is one to six weeks. The membrane 10 can be replaced when exhausted. Their cost varies from almost one hundred to several hundred dollars so they can not be called "disposable" and they have not been cost effective. Attempts at miniaturization to diameters of 1 to 2 mm have been less than successful, primarily because of difficulty in controlling the distribution of adhesive when attaching miniature membranes to the shank tube.

The performance of this electrode can be improved by the inclusion in the half cell structure of one or both of the materials silver black and platinum black. Only small quantities are required. Their inclusion increases stability and improves NERNSTIAN response.

Silver black and platinum black are comparable in effect when used alone, but the effect is enhanced when they are applied together. They can be used as substitutes for silver chloride although not identical to silver chloride in operation. Silver chloride has low d.c. polarization for measurement of d.c. current, but has high A.C. polarization. Platinum black exhibits the opposite effect.

These materials have the very great advantage that they can be incorporated in the metal-metal salt paste mixture that is sintered on the conductor wire to form the half cell, or they can be applied as coatings over the surface of the half cell and over one another. They are simply applied by dipping the half cell in a suspension of silver black in a carrier that is evaporated away. Similarly, the platinum black may be applied by dipping the half cell and its silver black coating in a suspension of platinum black. The carrier is then evaporated away to leave a platinum black overlayer.

The half cell of FIG. 2 was made by that process. It comprises a silver wire 32 whose end has been coated with a paste of silver and silver chloride particles. The paste was driven off and the silver and silver chloride particles were bonded to one another and to the wire by sintering. The half cell was dipped into a suspension of silver black and platinum black in tetrahydrofuran and a plasticizer. It was withdrawn and allowed to dry. In this case, the plasticizer was ethylene glycol. On removal, the half cell was dried to leave a layer of silver black and platinum black containing a small quantity of ethylene glycol.

The half cell so prepared is designated 34 in FIG. 2. It is drawn into the end of a protective tube 36 of PVC such that part of it protrudes. Thereafter, it is dipped into a potassium ion selective PVC membrane of the kind that is described above. It is dipped once or twice into that solution such that the protruding end of the half cell is covered and such that the end of the PVC tube is sealed. The PVC coating is dried to produce the electrode shown in FIG. 2.

The unit of FIG. 2 can be made in 2 to 3 mm diameter size, but its performance is not as good as the unit shown in FIG. 1 because it tends to drift. Nonetheless, it is very much better than a unit which omits the silver black and the platinum black, notwithstanding that those materials are formed in coatings over the basic half cell material rather than being mixed with them.

The electrode of FIG. 2 can be made to work as well and even better than the electrode of FIG. 1 by the addition of another layer of material. A layer of immobilized electrolyte is added between the half cell material and the outer, ion selective layer. That can be accomplished by adding a layer of hydrophilic or porous organic material over the half cell and then sealing that layer in place with the outer ion selective layer. Water can be added to this water absorbent layer (hereafter referred to as a hydrophilic layer) either before or after addition of the outer layer. If not included as part of the material of the electrolyte layer, water can be introduced through the outer layer as in the case of the electrode of FIG. 2. Electrodes which incorporate such an hydrophilic layer are shown in FIGS. 3 and 4. The hydrophilic layer is visible in FIG. 3 where it is designated 40. The outer layer 42 is formed of potassium selective PVC as described above. The layer 44 below the hydrophilic layer is platinum black. The layer 46 below that is silver black. Layer 48 is sintered silver and silver chloride bonded to a silver wire 50. This unit was constructed by forming the initial silver-silver chloride half cell and successively dipping it into a suspension of silver black and platinum black, hydrophilic gel material and the potassium selective PVC membrane solution.

Layer 40 was formed from a solution prepared as follows:

To a 100 ml solution of 4 mM KCl and 150 mM NaCl add:
3 g animal gelatin
2.5 ml polyethylene glycol
2 ml 10% silver nitrate solution.

While stirring, heat gently and allow the gelatin to dissolve. Then, add 10 ml of 40% formaldehyde.

The half cell was dipped in that mixture to cover under layers of half cell material and allowed to dry while the conductor wire was suspended end down.

The dashed line that separates the electrolytic layer 40 from the potassium selective layer 42 represents that there is no clear line of demarcation between the two as a consequence of the plasticizing action of the plasticizer.

When the bulbous sensor 60 has been produced and is dried, it may be mounted at the end of a supporting structure that facilitates the proposed application. In FIG. 4, the sensor bulb is shown to be fastened by an urethane adhesive material 62 into the end of a 2 millimeter outside diameter polyvinyl chloride tube 64 to form a needle shaped electrode thin enough to be inserted into a patient's bloodstream.

The whole of the unit is depicted in FIG. 5 where the tube 64 extends into a handle portion 66 from which a shielded conductor 68 extends.

That the invention is applicable to other physical arrangements is depicted in FIG. 6 where it is housed in a package suitable for industrial application. However, it is the in vivo, potassium level application that is most interesting. The needle shaped electrode of FIGS. 3, 4 and 5 can be mass manufactured and produced at a small fraction of the cost of the electrode of FIG. 1. It can be inserted into a patient and used to monitor potassium level during an operative procedure. It will maintain its calibration and the sensor may simply be left in place while the patient is moved from the operating room to a critical care unit or intensive care room. When no longer needed by the patient, it is disposed.

An important element in the electrolyte layer is the hydrophilic or porous organic material. It may have a variety of forms. The requirement is that it accept and retain an electrolyte. In preferred form, it should be reduceable to a liquid or semi-liquid that permits its being coated on a half cell in a dipping or spraying process and then dried sufficiently to permit subsequent addition of an over layer of ion selective membrane material preferably by dipping or spraying.

It is advantageous to have water contained in the electrolyte layer so that prolonged soaking is not required prior to use. On the other hand, it matters not whether the water is included in the hydrophilic layer when applied or is added later. Thus, for example, the hydrophilic material might be a readily wetted expanded plastic which is dry after being applied over the half cell material. Water could be added to such a material just prior to addition of the ion selective overmaterial. It now appears, however, that the form most likely to permit close control of quality, and that is least expensive to produce, is to form the electrolyte layer as a gel. A wide variety of suitable gels is available. Animal gels are satisfactory. A variety of resins are commercially available in gel form and are likely to be more uniform.

In FIG. 7, the reference electrode for use in the method of the invention comprises a metal wire 70 on the active end 77 of which is a coating 72 of the salt of that metal. A preferred form employs a silver wire as the wire 70. The inner coating 72 is silver chloride with an overlayer 74 of silver black and platinum black, and an outer layer of protein material 76. Thus, the reference electrode is equivalent to the silver wire 50 and silver chloride covering 48, and the silver black and platinum black coatings 44 and 46 of FIG. 3.

In the preferred form, the material of the reference electrode half cell and the ion selective half cell are the same. In most cases, both will have silver chloride bonded to a silver wire. If one has a coating of silver black, so should the other. If one includes platinum black, so should the other.

In the preferred form, the reference electrode is "prepoisoned" by being coated with a very thin layer of protein. That can be accomplished by soaking the otherwise completed reference cell in animal gelatin for an hour or two.

The electrode of FIGS. 3 and 7 are combined in a catheter structure 78 in FIG. 8. The showing here is schematic. A flexible triple tube 80 is formed with three openings which extend in parallel over the length of the tubing. One end is fastened to an end fitting 82 and the other end is cut off on the bias as best shown in FIG. 8. The three openings are numbered 83, 84 and 85 for identification. The sensor of FIG. 3 is shown disposed in opening 83. Its multilayered sensing end 60 is exposed at the cut end of the tubing 80. The silver wire 50 extends through the opening 83 back to the connector 82. A plug 86 of epoxy fixes the selective sensor 60 in place and seals the opening. Another plug 88 of epoxy fixes the reference electrode in place in opening 84 with the silver chloride body exposed at the cut end of the tube. The other opening 85 serves as the catheter opening.

The reference electrode and the ion selective sensing electrode are connected to the shield braid and the center conductor, respectively, of a coaxial cable at the connector 82. When inserted into a sample solution, the two electrodes permit measurement of the potential across the ion selective membrane of the sensing electrode at the analyzer to which the coaxial cable is connected.

A two-channel analyzer is depicted in FIG. 10. The instrument shown is arranged to measure potassium level in an unknown sample or in a known standard solution. It matters not whether the analyzer is formed by two separate single channel instruments or is a single instrument which operates on a time share basis to provide two separate channels. What is important, is that the two channels provide substantially accurate and corresponding indications when used to measure the same sample.

In the instrument 100 shown, the display 102, the input terminal 104, and the calibration or scale control 106 are part of the channel that is to be used to measure unknown samples. The display 102 is labelled "PATIENT." The other channel has a display 108 marked "STAT," a calibration or scale control 110 and a coaxial cable input 112.

In the drawing the combination electrode catheter 78 is shown to be inserted into a standard solution tube 114 and to be connected by a coaxial cable 116 to input connector 112 of the calibration channel. The standard solution tube 114 contains a body 120 of 4.0 m Eq. K/L solution as indicated by the numerals in the display 108. The calibration knob 110 was rotated until those numerals appeared in the display 104.

The other sample tube 122 contains a quantity of blood 124. If the combination electrode catheter 78 is moved from tube 114 and is inserted in the blood in tube 122, and if the calibration knob 110 is not moved, the display 108 will change to display the level of potassium in the blood sample 124. In this example, let it be assumed that the numerals 3.85 appeared in display 108 when measuring the potassium level in sample 124.

Instead of a catheter mounted combination electrode 78, separate ion selective and reference electrodes are to be used to measure potassium level in the blood of a patient being dialyzed. The flow cell 130 is assumed to be connected in series in the bypass by which the patient's blood is delivered to and returned from the dialysis machine. The potassium ion selective electrode 132 and the reference electrode 134 are mounted at closely adjacent points of the cell. Both electrodes are arranged to extend into the blood flow. Except that they are packaged differently, the ion selective electrode 132 is like the electrode of FIG. 3 and the reference electrode is like the electrode of FIG. 7. Thus, they are like the corresponding electrodes in catheter unit 78.

The two electrodes 132 and 134 are connected to the center conductor and shield braid, respectively, of a coaxial cable 136 which is connected to the sample channel input 104. Since the blood measured by electrodes 132 and 134 in the cell is the same as the blood sample 124, it, too, must have 3.85 millileters equivalent potassium per liter if the sample 124 was drawn shortly before and if there was no intervening event which could have changed the potassium level. All that remains is to turn the calibration knob 106 until the numerals in the "PATIENT" display 102 are 3.85. Thereafter, the display 102 will change only if the potassium level in the blood has changed. The catheter 78 is left in the standard solution 120. The "STAT" display 104 will continue to display 4.0. If the surgeon or the intensive care nurse wants to verify that the displayed value of potassium level is correct, a blood sample 124 is drawn and placed in a clean container 122, and the electrode assembly 78 is transferred from the reference solution 120 in tube 114 to the blood sample in tube 122. The reading at display 108 should be the same as that appearing at the patient display 102. If there is a difference in the readings, it is patient display 102 which is then adjusted. The indwelling electrode is now calibrated without having removed it from, and replacing it back into, the patient.

In FIG. 11, the transparent, plastic package 140 is evacuated so that it fits tightly against the flow cell 142 contained inside the package. A reference electrode 144 and an ion selective electrode 146 are mounted in openings along the length of the cell. Plastic disposable caps 148 and 150 seal the ends of the cell which is filled with a body 152 of reference or calibration solution. The conductor terminals 154 and 156 extend out of the package 140 and are bonded by a pressure adhesive to the upper margin of the package to preserve the sterility of the interior. By this means the electrodes are presoaked. They can be converted to the analyzer and the latter calibrated without opening the package. When ready for use, the package is torn open to provide access to the cell. The end caps are removed and the cell is inserted in a flow line. Thereafter, the package is removed entirely or, in certain environments in which it is desirable not to expose any adhesive, all but the portion 160 around the electrodes in removed.

Figure 12:
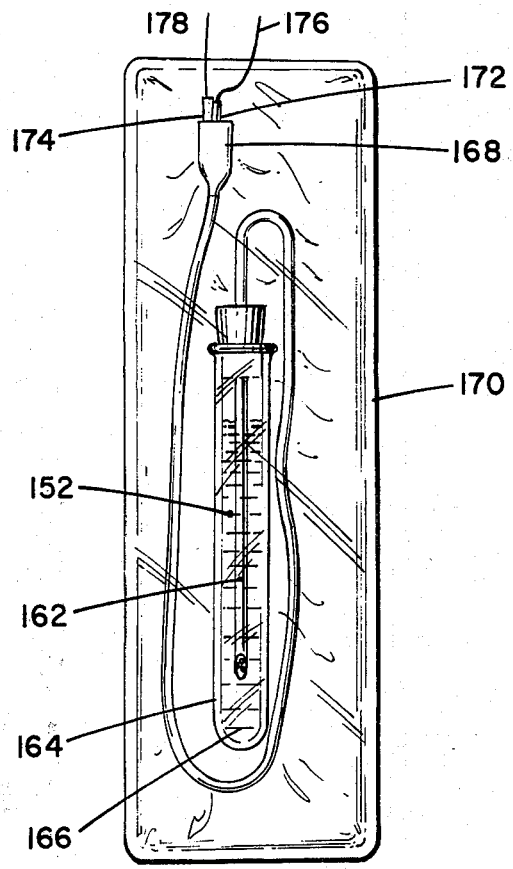
FIG. 12 is a view in front elevation, and partly in section, of a combination electrode in catheter form disposed in a reference solution and a sterile package.

FIG. 12 shows a similar arrangement except that the two electrodes are mounted together as a combination electrode 162 in a flexible catheter. The active portions are disposed in a vial 164 filled with a reference liquid 166. The stopper of the vial is slid along the catheter tube back to the connector block 168 when the sterile package 170 is opened. In this case, separate temporary connectors 172 and 174 are attached to the terminals of block 168. Lead wires 176 and 178 extend from the package to permit calibration before the package is opened. In this case, the package is not evacuated.

Although I have shown and described certain specific embodiments of my invention, I am fully aware that many modifications thereof are possible. My invention, therefore, is not to be restricted except insofar as is necessitated by the prior art.

I claim:

1. An ion selective electrode comprising a metallic conductor, an overlayer of at least one of silver black or platinum black overlying the conductor, a layer of non-liquid hydrophilic material overlying and in intimate contact with said overlayer and a material selective to a specific ion and overlying and in intimate contact with the hydrophilic material.

2. The invention defined in claim 1 in which said material comprises a hydrophobic polymer and in which the hydrophobic material is a gel containing salt and a plasticizer.

3. The invention defined in claim 2 in which said polymer includes a substance selected from the group consisting of monactin, nonactin, gramicidins, valinomycin and mixtures thereof, and is selective to the potassium ion.

4. The invention defined in claim 1 in which said hydrophilic material comprises a mixture of a salt and gelatin.

5. The invention defined in claim 1 which further comprises a reference electrode formed by a metal wire covered with whichever of platinum black and silver black that is incorporated in said overlayer; and
means for mechanically connecting said reference electrode and said ion electrode for insertion together into a common solution while maintaining them electrically isolated except through the solution.

6. The invention defined in claim 5 in which said means for mechanically connecting the electrodes comprise a multiple, parallel passage tubing, the reference electrode being associated with one passage of the tubing and the ion selective electrode being associated with a different passage of the tubing.

7. An ion selective electrode comprising a metal-metal salt half cell, a layer of nonliquid hydrophilic material overlying and in intimate contact with the half cell, a material selective to a specific ion and overlying and in intimate contact with the hydrophilic material; said half cell comprising silver and silver chloride and further comprising both silver black and platinum black.

8. An ion selective sensing electrode comprising:
a wire conductor, a portion of which is coated with at least one of silver black and platinum black;
means in the form of a water and salt bearing hydrophilic coating of water absorbing substance overlying said coating for forming an immobilized electrolytic layer on said half cell; and
an encasing, ion selective protective layer of hydrophobic polymer containing an ion selective material overlying said hydrophilic coating.

9. The invention defined in claim 8 in which said encasing, ion selective protective layer is the product of a dipping process in which the half cell and overlying electrolytic layer are dipped into a body of liquid containing said hydrophobic polymer.

10. The invention defined in claim 9 in which said electrolytic layer is the product of a dipping process in which the half cell is dipped into a body of liquid containing said water absorbing substance.

11. The invention defined in claim 8 in which said half cell is formed at the end of a conductor and in which said electrolytic layer of material and its encasing ion selective protective layer forms a solidified bulbous body at the end of said conductor.

12. The invention defined in claim 11 in which said electrode further comprises a tubular sheath surrounding said conductor and from whose end said bulbous body extends whereby to form a needle shaped structure.

13. The invention defined in claim 8 in which the ion selective layer includes a solvent which will partially dissolve the outer surfaces of the electrolytic layer.

14. In combination, an ion selective electrode and a reference electrode, each comprising reference electrode, each comprising a half-cell formed of like material, the half-cell of each electrode comprising at least one of silver black and platinum black and the reference electrode being overcoated with a layer of protein material; said electrodes, except for portions of their electrical conductors, being disposed in a common sealed container containing reference solution.

15. The invention defined in claim 14 in which the sealed container of reference solution is contained within a sealed package.

* * * * *